US006995020B2

(12) United States Patent
Capodieci et al.

(10) Patent No.: US 6,995,020 B2
(45) Date of Patent: Feb. 7, 2006

(54) METHODS AND COMPOSITIONS FOR THE PREPARATION AND USE OF FIXED-TREATED CELL-LINES AND TISSUE IN FLUORESCENCE IN SITU HYBRIDIZATION

(75) Inventors: Paola Capodieci, New York, NY (US); Jon Edelson, Scarsdale, NY (US)

(73) Assignee: Aureon Laboratories, Inc., Yonkers, NY (US)

( * ) Notice: Subject to any disclaimer, the term of this patent is extended or adjusted under 35 U.S.C. 154(b) by 0 days.

(21) Appl. No.: 10/624,233

(22) Filed: Jul. 21, 2003

(65) Prior Publication Data

US 2005/0019779 A1    Jan. 27, 2005

(51) Int. Cl.
*G01N 33/00* (2006.01)
*C12M 1/34* (2006.01)
*C07H 21/00* (2006.01)

(52) U.S. Cl. .................... 436/94; 435/287.2; 536/23.1

(58) Field of Classification Search .................... 435/6, 435/91.1, 187, 287.2; 536/23.1, 24.31; 436/94

See application file for complete search history.

(56) References Cited

U.S. PATENT DOCUMENTS 6,580,056 B1    6/2003    Tacha
2004/0038270 A1 *  2/2004  Muhlhahn et al. ............. 435/6

OTHER PUBLICATIONS

Engel et al., Journal of Clinical Pathology, Jan. 1997, vol. 50, No. 1, pp. 37-39.*
Baschong et al., The Journal of Histochemistry & Cytochemistry, 2001, vol. 49, No. 12, pp. 1565-1571.*
International Search Report corresponding to PCT/US04/23207 mailed Sep. 19, 2005.

* cited by examiner

*Primary Examiner*—Bradley L. Sisson
(74) *Attorney, Agent, or Firm*—Richard G. Gervase, Esq.; Mintz Levin Cohn Ferris Glovsky and Popeo PC

(57) ABSTRACT

This invention relates to methods for the detection of one or more mRNA transcripts in paraffin-embedded tissue by "mRNA liberation in fixed-treated tissue or 'MLIFTT'". This method includes treating the tissue with ammonia-ethanol and sodium borohydride combined with pressure cooking of the tissue. The chemical treatments reduce the tissue autofluorescence and the physical treatments overcome the interference created by the fixation-induced chemical bonds. The methods of the present invention can be utilized to identify a plurality of mRNA transcripts in a microarray format.

7 Claims, 1 Drawing Sheet

METHODS AND COMPOSITIONS FOR THE PREPARATION AND USE OF FIXED-TREATED CELL-LINES AND TISSUE IN FLUORESCENCE IN SITU HYBRIDIZATION

FIELD OF THE INVENTION

This invention relates to the fields of molecular biology, medicine diagnostics. This invention particularly relates to methods for preparing and using fixed-treated cell lines and tissue in fluorescence in situ hybridization.

BACKGROUND OF THE INVENTION

Advancements in the understanding of gene expression and epidemiology combined with developments in technology have allowed for the correlation of genetic expression with, for example, disease states. An accurate correlation may enable risk assessment for an individual based on the expression profile of their individual cells. Further, drug screening and other research based protocols may quickly generate data in cell lines or tissue samples that can be extended to develop treatments for human disease. However, most of the methodologies available for evaluation of cell lines or tissue have well-known drawbacks. For example, methods that require disaggregation of the sample, such as Southern, Northern, or Western blot analysis, are rendered less accurate by dilution of the malignant cells by the normal or otherwise non-malignant cells that are present in the same sample. Furthermore, the resulting loss of tissue architecture precludes the ability to correlate, for example, malignant cells with the presence of genetic abnormalities in a context that allows morphological specificity. This issue is particularly problematic in tissue types known to be heterogeneous, such as in human breast carcinoma, where a significant percentage of the cells present in any area may be non-malignant.

Another drawback is that many of the art recognized techniques require the tissue being analyzed to be fresh. Typically, however, it is not always possible in the clinical setting to work on cell lines or tissue as soon as they are available.

Accordingly, cell lines or tissue are often preserved in paraffin. Processes for treating a paraffin-embedded tissue sample for gene analysis have been described, for example, U.S. Pat. Nos. 5,672,696 and 6,248,535. Typically treatments comprise treating tissue cells freed of paraffin with a solution containing a surfactant, a protease, etc. at room temperature to upwards of 60° C. for 4 to 48 hours to disrupt the tissue cells, removing impurities (i.e., substances other than nucleic acid) by a two-phase separation method (i.e., a method comprising separation into an aqueous phase containing the nucleic acid and an organic solvent phase containing denatured protein and the like by addition of one or more organic solvents such as phenol, chloroform, etc.), and then adding an alcohol to the residue to precipitate the nucleic acid in the aqueous phase (Jikken Igaku, Vol. 8, No. 9, pp 84–88, 1990, YODOSHA CO., LTD.). While this technique allows for the analysis of gene expression, the purification disrupts cellular architecture and does not allow the application of in situ hybridization techniques.

As described in U.S. Pat. Nos. 5,750,340 or 6,165,723, in situ hybridization (ISH) is a powerful and versatile tool for the detection and localization of nucleic acids (DNA and RNA) within cell or tissue preparations. By the use of labeled DNA or RNA probes, the technique provides a high degree of spatial information in locating specific DNA or RNA target within individual cells or chromosomes. ISH is widely used for research and potentially for diagnosis in the areas of prenatal genetic disorders, and molecular cytogenetics. In the general area of molecular biology, ISH is used to detect gene expression, to map genes, to identify sites of gene expression, to localize target genes, and to identify and localize various viral and microbial infections. Currently, the application of the ISH technology research is being expanded into tumor diagnosis, preimplantation genetic diagnosis for in vitro fertilization, evaluation of bone marrow transplantation, and analysis of chromosome aneuploidy in interphase and metaphase nuclei.

In ISH, labeled nucleic acids (DNA or RNA) are hybridized to chromosomes, DNA or mRNAs in cells which are immobilized on microscope glass slides (In Situ Hybridization: Medical Applications (eds. G. R. Coulton and J. de Belleroche), Kluwer Academic Publishers, Boston (1992); In Situ Hybridization: In Neurobiology; Advances in Methodology (eds. J. H. Eberwine, K. L. Valentino, and J. D. Barchas), Oxford University Press Inc., England (1994); In Situ Hybridization: A Practical Approach (ed. D. G. Wilkinson), Oxford University Press Inc., England (1992)). Numerous non-isotopic systems have been developed to visualize labeled DNA probes including, for example, a) fluorescence-based direct detection methods, b) the use of digoxigenin- and biotin-labeled DNA probes coupled with fluorescence detection methods, and c) the use of digoxigenin- and biotin-labeled DNA probes coupled with antibody-enzyme detection methods. When fluorescence-labeled nucleic acid (DNA or RNA) probes are hybridized to cellular DNA or RNA targets, the hybridized probes can be viewed directly using a fluorescence microscope. By using multiple nucleic acid probes with different fluorescence colors, simultaneous multicolored analysis (i.e., for multiple genes or RNAs) can be performed in a single step on a single target cell (Levsky et al. Science 2001). Fluorochrome-directly labeled nucleic acid probes eliminate the need for multi-layer detection procedures (e.g., antibody-based system), which allows for fast processing and also reduces non-specific background signals. Therefore, fluorescence in situ hybridization (FISH) has become an increasingly popular and valuable tool in both basic and clinical sciences.

Unfortunately, although FISH is an extremely useful technique, detection of mRNA, especially pre-mRNA, in paraffin-embedded or otherwise fixed-treated cell lines or tissue (i.e., "fixed-treated tissue" defined as tissue that is not fresh frozen) is currently difficult, if not impossible. FISH is a highly sensitive assay that allows the detection of nucleic acid within undisturbed cellular and tissue architecture and the use of synthetic oligomer probes in FISH has improved the sensitivity of the process; however, to date FISH has only been successfully conducted in cells grown through cell-line culture. mRNA detection through FISH has not been successfully conducted in tissue until just recently (Nguyen et al., J Biol Chem, November 1;277(44):41960–9 (2002)); Paris et al., Science, July 13;293 (5528):293–7 (2001)).

Detection is difficult for a number of reasons, including interference caused by the creation of chemical bonds during fixation processes as well as native autofluorescence in the cell lines or tissue. The ability to easily apply FISH to such cell lines or tissue would be of great interest because of the large amount of clinically relevant cell lines and tissue that have been (and continue to be) preserved in this fashion.

U.S. Pat. No. 5,856,089 describes in situ hybridization methods using nucleic acid probes for single copy sequences for detecting chromosomal structural abnormalities in fixed tissue obtained from a patient suspected of having a chromosomal structural abnormality. The methods include the use of bisulfite ion on the fixed cells.

U.S. Pat. No. 5,672,696 describes preparation of a sample for a gene analysis or high-purity nucleic acid suitable for gene amplification from a paraffin-embedded tissue sample comprising heating an aqueous suspension containing a surfactant having a protein-denaturation action and a deparaffinized tissue sample obtained from a paraffin-embedded tissue sample at 60° C. or higher. However, it is not an-object of this patent to preserve the cellular architecture.

FISH has historically been combined with classical staining methodologies in an attempt to correlate genetic abnormalities with cellular morphology [see e.g., Anastasi et al., Blood 77:2456–2462 (1991); Anastasi et al., Blood 79:1796–1801 (1992); Anastasi et al., Blood 81:1580–1585 (1993); van Lom et al., Blood 82:884–888 (1992); Wolman et al., Diagnostic Molecular Pathology 1(3): 192–199 (1992); Zitzelberger, Journal of Pathology 172:325–335 (1994)]. However, several of these studies address hematological disorders where genetic changes are assessed in freshly fixed smears from bone marrow aspirates or peripheral blood specimens. U.S. Pat. No. 6,573,043 describes combining morphological staining and/or immunohistochemistry (IHC) with fluorescence in situ hybridization (FISH) within the same section of a tissue sample.

U.S. Pat. No. 6,534,266 describes an in situ hybridization method for detecting and specifically identifying transcription of a multiplicity of different target sequences in a cell. The method includes assigning a different bar code to at least five target sequences, with each target sequence containing at least one predetermined subsequence. Each bar code contains at least one fluorochrome, and at least one bar code comprises at least two different, spectrally distinguishable fluorochromes. A probe set specific for each target sequence is provided in the method. Each probe set contains a hybridization probe complementary to each subsequence in the target sequence. Each probe is labeled with a fluorochrome, and the fluorochromes in each probe set collectively correspond to the bar code for the target sequence of that probe set. Similar techniques are envisioned in combination with the invention disclosed herein.

Further, although spotted chip expression microarrays have been used extensively to detect the presence or absence of multiple specific mRNAs simultaneously in tissue, to date the effective application of this technique has been limited to fresh frozen tissue and does not describe an easy application utilizing paraffin-embedded or other fixed-treated tissue (for example, see United States Patent Publication Nos. 20030040035 and 20020192702). Because much of the cell lines and tissue available for scientific or medical study has been fixed, the ability to effectively use spotted chip arrays on fixed-treated cell lines and tissue would be of great potential value in (1) the discovery of the molecular mechanisms of the cell and its surrounding tissue in health and disease, (2) the creation of tests diagnostic of disease, (3) the creation of treatments therapeutic for disease, and (4) the identification of agents that are toxic to cells. Therefore, the present invention fulfills a need in the art by providing, for example, a process termed "mRNA liberation in fixed treated tissue or 'MLIFFT'" to enable the detection of mRNA, especially pre-mRNA, in fixed treated tissue.

SUMMARY OF THE INVENTION

As will be understood by one of skill in the art, in one aspect the present invention provides a method for rendering fixed treated cell-lines and tissue (i.e. paraffin embedded tissue) susceptible to further analysis using fluorescence detection methods. Such methods were formally not compatible with fixed treated cell lines or tissue. This invention, therefore, provides a method and composition which will be useful in a range of protocols as will be apparent to one of skill in the art. While several of these protocols will be herein described, such description is not meant in any way to limit the applicability of the current invention. In one aspect, the invention provides a method of reducing autofluorescence in a sample during FISH. The process comprises treating the cell-lines or tissue with ammonia-ethanol and sodium borohydride and pressure cooking prior to performing FISH.

In one aspect, the invention provides a method, termed MLIFTT, to enable the detection of mRNA, especially pre-mRNA, in fixed-treated cell lines or tissue. The invention also describes the linkage of the MLIFTT process to enable the detection of one or more specific mRNAs in fixed-treated cell lines or tissue through the process of fluorescence in situ hybridization ("Tissue-FISH") with or without quantitative computational fluorescence microscopic analysis. Such linkage allows the use of fixed treated cells in the evaluation of toxicological or therapeutic responses to agents which were administered to the cells prior fixation. The invention also describes the linkage of the MLIFTT process to microarray analyses using fixed-treated cell lines or tissue. The invention also describes the linkage of the MLIFTT process to enable other potential measurements.

In one aspect, the invention provides a process to treat cell lines or tissue for the specific purpose of detecting mRNA, especially pre-mRNA. The process comprises treating the cell lines or tissue with ammonia-ethanol and sodium borohydride and pressure cooking the cell lines or tissue to achieve improved detection of mRNA. Without being bound by theory, it is thought that the chemical treatments reduce the auto-fluorescence of the cell lines or tissue and the physical treatments overcome interference created by the fixative-induced chemical bonds.

In another aspect, the invention combines a method to pre-treat the cell lines or tissue with advances in computational fluorescence microscopy with specialized probes designed to visualize expression of one or many genes simultaneously inside single cells (either alone or within a tissue). Single-cell expression profiling is valuable because it enables the simultaneous detection of the presence (or absence) of multiple molecular entities or "markers" within the cell. The presence (or absence) of these molecular entities characterizes and provides insight into the regulatory activity of each cell. The detection of these entities has potential value in (1) the discovery of the molecular mechanisms of the cell and its surrounding tissue in health and disease, (2) the creation of tests that are diagnostic of disease, (3) the identification of agents that are therapeutic for disease, and (4) the identification of agents that are toxic to cells.

In another aspect, the invention provides a process combining the pre-treatment of the cell lines or tissue by chemical and physical processes followed by the detection of specific pre-mRNA transcript(s) through specific fluorochrome-labeled oligo-probes ("Tissue-FISH"). The pre-treatment process is the treatment of the cell lines or tissue with ammonia-ethanol and sodium borohydride and pressure cooking the cell lines or tissue. Following the treatment, specific probes are applied to the cell lines or tissue to detect specific pre-mRNA transcripts. The specific probes have fluorochromes which can be detected through quantitative computational fluorescence microscope analysis. In this way, an individual could simultaneously detect multiple specific pre-mRNA entities in a single cell. The limit of the number of specific pre-mRNA entities is limited only by the number of unique available fluorochromes that can be attached to these probes.

In another aspect, the invention provides a pre-mRNA labeling technique that can increase the number of molecular entities that may be simultaneously detected beyond the number of uniquely (or spectrally distinct) available fluorochromes. This feature of the invention is to create and apply multiple oligo-probes to the cell lines or tissue which are specific for a pre-mRNA transcript that, when attached to their target pre-mRNA, create a unique fluorescent barcode for each transcript. These barcodes can then be detected using quantitative computational fluorescence microscopic analysis. The number of potential pre-mRNA transcripts that can be simultaneously detected has been increased from the number of available unique fluorochromes ("n") to n raised to the power of the number of fluorochrome-unique probes that can be created for a specific pre-mRNA.

In another aspect, the invention provides a method to quantify the level of specific pre-mRNA expression by using a computerized detection system to quantify the level of attached fluorochrome labeling by measuring the intensity of the fluorochrome signal. The level of specific pre-mRNA expression is calculated by assuming it is proportional to the level of intensity of the fluorochrome signal. In another aspect, the invention includes a process of combining the pretreatment of the fixed-treated cell lines or tissue by chemical and physical processes followed by the detection of specific mRNA transcript(s) through spotted chip arrays. The pre-treatment process is the treatment of the cell lines or tissue with ammonia-ethanol and sodium borohydride and pressure cooking the cell lines or tissue. Following this pre-treatment of the fixed-treated cell lines or tissue, the cell lines or tissue is disrupted and then applied to spotted chip arrays to detect the presence and level (or absence) of specific mRNAs.

In yet another aspect, the invention provides a process of measuring the presence or absence or quantified amount of specific pre-mRNA and/or mRNA using probes to detect these entities in (i) cell lines or (ii) cell lines or tissue from animals or (iii) cell lines or tissue from humans, to determine if the respective cell lines or tissue, when treated with a test compound, displays a gene expression profile indicating a potential therapeutic or toxic activity for the test compound. Such effects would be revealed by differences in pre-mRNA or mRNA expression between the treated and untreated cell lines or tissue. Probes can be designed, for example, to specifically target known therapeutic or toxicologic pathways. This process could be conducted on culture cell lines or fresh frozen cell lines or tissue or fixed cells or fixed tissue. If this process is conducted on fixed cells or fixed tissue, the MLIFTT process could be employed to liberate the pre-mRNA or mRNA for measurement. FISH applied to cell lines or Tissue-FISH applied to cell lines could be used to enable the measurement of the pre-mRNA or mRNA. To make the measurement more effective and valuable, multiplexed FISH applied to cell lines or Tissue-FISH could be used to measure multiple pre-mRNAs or mRNAs simultaneously in the same sample of cell lines or tissue. This would be more valuable because it 1) more efficiently uses potentially scarce cell lines and tissue as well as expensive reagents, 2) saves time, and 3) allows investigators to see the simultaneous interrelationships of gene expression more clearly in single cells or groups of cells.

DETAILED DESCRIPTION OF THE INVENTION

Figure 1:
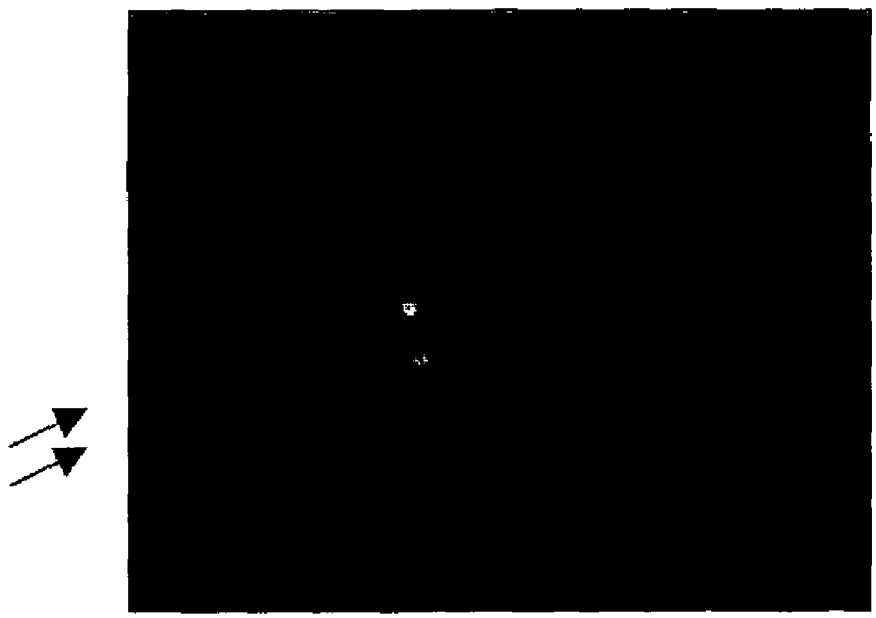
FIG. 1: Detection of SMG-1 gene on Paraffin-embedded prostate Carcinoma using Cy3 and Cy5 labeled probe (arrows are pointing at two transcription sites).

Before the present methods, kits and uses therefore are described, it is to be understood that this invention is not limited to the particular methodology, protocols, cell lines, animal species or genera, constructs, and reagents described which may be modified or substituted as would be known to one of skill in the art. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "and", and "the" include plural referents unless the context clearly dictates otherwise. Thus, for example, reference to "a genetic alteration" includes a plurality of such alterations and reference to "a probe" includes reference to one or more probes and equivalents thereof known to those skilled in the art, and so forth.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All patents and publications mentioned herein are incorporated herein by reference in their entirety.

Publications cited herein are cited for their disclosure prior to the filing date of the present application. Nothing here is to be construed as an admission that the inventors are not entitled to antedate the publications by virtue of an earlier priority date or prior date of invention. Further the actual publication dates may be different from those shown and require independent verification.

As will be understood by one of skill in the art, in one aspect the present invention provides a method for rendering fixed treated cell-lines and tissue (i.e. paraffin embedded tissue) susceptible to further analysis using fluorescence detection methods. Such methods were formally not compatible with fixed treated cell lines or tissue. This invention, therefore, provides a method and composition which will be useful in a range of protocols as will be apparent to one of skill in the art. While several of these protocols will be herein described, such description is not meant in any way to limit the applicability of the current invention.

The present invention is directed, in part, towards improved methods for directly detecting the presence of a target nucleic acid in cells of paraffin-embedded or otherwise fixed-treated cell lines or tissue, a process termed "mRNA liberation in fixed-treated tissue or 'MLIFTT'". More specifically, novel improvements of the traditional fixative/pretreatment methods are described which employ treatment of the tissue with ammonia-ethanol and sodium borohydride and pressure cooking the tissue to achieve improved detection of pre-mRNA.

As used herein, "Tissue-FISH" refers to the use of fluorescent labeled probes, for example, of up to approximately 50 bp in the detection of nucleic acids in paraffin embedded tissue samples.

One of skill in the art will understand that, with respect to the instant invention, references to tissue are generally equally applicable to cell lines. Accordingly, although one term may be used with respect to a particular method, it should be understood that the composition or method applies equally to the other. In referring generally to the types of material that may be utilized according to the invention, the inventors may use terms like "sample" etc.

As used herein, "fluorochrome" refers to a particular fluorescent dye, e.g., Cy3, Cy5, without regard to number of individual dye molecules, and without regard to chemical conjugation.

As used herein, "fluorophore" refers to an individual fluorescent dye molecule or conjugated moiety.

As used herein, the term "nucleic acid" refers to DNA, RNA, or the equivalent thereof, including pre-mRNA, cDNA, chromosomal, mitochondrial, viral and/or bacterial nucleic acids. The term "nucleic acid" encompasses either or both strands of a double stranded nucleic acid molecule and includes any fragment or portion of an intact nucleic acid molecule.

As used herein, the term "probe" refers to synthetic or biologically produced nucleic acids that are engineered to contain specific nucleotide sequences which hybridize under stringent conditions to target nucleic acid sequences.

As used herein, a "labeled probe" is defined as a probe which is prepared with a marker moiety for detection. The marker moiety is attached at either the 5' end, the 3' end, internally, or in any possible combination thereof. The preferred moiety is an identifying label such as a fluorophore. The labeled probe may also be comprised of a plurality of different nucleic acid sequences each labeled with a marker moiety. It may be beneficial to label the different nucleic acid sequences each with a different marker moiety.

By "subject" or "patient" is meant any single subject for which therapy is desired, including humans, cattle, dogs, guinea pigs, rabbits, chickens, insects and so on. Also intended to be included as a subject are any subjects involved in clinical research trials not showing any clinical sign of disease, or subjects involved in epidemiological studies, or subjects used as controls.

"Toxicology analysis" as used herein refers to protocols directed towards identifying, for example, genetic expression (or lack thereof) indicative of a toxic response by the cell to, for example, an agent. Toxicological response pathways are familiar to those of skill in the art.

By "tissue sample" is meant a collection of similar cells obtained from a tissue of a subject or patient, preferably containing nucleated cells with chromosomal material. The four main human tissues are (1) epithelium; (2) the connective tissues, including blood vessels, bone and cartilage; (3) muscle tissue; and (4) nerve tissue. The source of the tissue sample may be solid tissue as from a fresh, frozen and/or preserved organ or tissue sample or biopsy or aspirate; blood or any blood constituents; bodily fluids such as cerebral spinal fluid, amniotic fluid, peritoneal fluid, or interstitial fluid; cells from any time in gestation or development of the subject. The tissue sample may also be primary or cultured cells or cell lines. The tissue sample may contain compounds which are not naturally intermixed with the tissue in nature such as preservatives, anticoagulants, buffers, fixatives, nutrients, antibiotics, or the like. In one embodiment of the invention, the tissue sample is "non-hematological tissue" (i.e. not blood or bone marrow tissue).

For the purposes herein a "section" of a tissue sample is meant a single part or piece of a tissue sample, e.g. a thin slice of tissue or cells cut from a tissue sample. It is understood that multiple sections of tissue samples may be taken and subjected to analysis according to the present invention, provided that it is understood that the present invention comprises a method whereby the same section of tissue sample is analyzed at both morphological and molecular levels, or is analyzed with respect to both protein and nucleic acid.

As used herein, "cell line" refers to a permanently established cell culture that will proliferate given appropriate fresh medium and space.

By "correlate" or "correlating" is meant comparing, in any way, the performance and/or results of a first analysis with the performance and/or results of a second or further analysis. For example, one may use the results of a first analysis in carrying out the second analysis and/or one may use the results of a first analysis to determine whether a second analysis should be performed and/or one may compare the results of a first analysis with the results of a second analysis. With respect to the embodiment of morphological analysis followed by FISH, one may use the results obtained upon morphological staining to determine area(s) of a tissue section which are normal and/or area(s) which are cancerous. Thus, histological normal area(s) in a heterogeneous tumor biopsy may be used as internal normal control(s).

By "gene" is meant any nucleic acid sequence or portion thereof with a functional role in encoding or transcribing a protein or regulating other gene expression. The gene may consist of all the nucleic acids responsible for encoding a functional protein or only a portion of the nucleic acids responsible for encoding or expressing a protein. The nucleic acid sequence may contain a genetic abnormality within exons, introns, initiation or termination regions, promoter sequences, other regulatory sequences or unique adjacent regions to the gene.

By "genetic abnormality" is meant a deletion, substitution, addition, translocation, amplification and the like relative to the normal native nucleic acid content of a cell of a subject.

By "disease gene" is meant a gene that results in altered protein product (i.e., protein different from native protein in terms of sequence, structure and/or amount expressed) and results in a disease.

By "deletion" is meant the absence of all or part of a gene.

By "amplification" is meant the presence of one or more extra gene copies in a chromosome complement.

The word "label" when used herein refers to a compound or composition which is conjugated or fused directly or indirectly to a reagent such as a nucleic acid probe or an antibody and facilitates detection of the reagent to which it is conjugated or fused. The label may itself be detectable (e.g., radioisotope labels or fluorescent labels) or, in the case of an enzymatic label, may catalyze chemical alteration of a substrate compound or composition which is detectable.

The term "fluorescent labeled nucleic acid probe" refers to a probe comprising (1) a nucleic acid sequence tagged with a fluorescent dye (2) capable of hybridizing with a target nucleic acid sequence.

By "morphological stain" is meant a dye that stains different cellular components, in order to facilitate identification of cell type and/or disease state by light microscopy. Preferably, the morphological stain is readily distinguishable from any label used in the FISH analysis, e.g., a stain which will not autofluoresce at the same wavelength as the fluorochrome used in the FISH analysis.

The term "antibody" is used in the broadest sense and specifically covers monoclonal antibodies, polyclonal antibodies, multispecific antibodies (e.g., bispecific antibodies), and antibody fragments so long as they bind specifically to a target antigen.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations that typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. The "monoclonal antibodies" may also be isolated from phage antibody libraries using the techniques described in Clackson et al., Nature 352:624–628 (1991) and Marks et al., J. Mol. Biol. 222:581–597 (1991), for example.

The monoclonal antibodies herein specifically include "chimeric" antibodies 10 (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity [U.S. Pat. No. 4,816,567; and Morrison et al., Proc. Natl. Acad. Sci. USA 81:6851–6855 (1984)].

The term "primary antibody" herein refers to an antibody which binds specifically to 20 the target protein antigen in a tissue sample. A primary antibody is generally the first antibody used in an immunohistochemical procedure. In one embodiment, the primary antibody is the only antibody used in an IHC procedure.

The term "secondary antibody" herein refers to an antibody which binds specifically to a primary antibody, thereby forming a bridge between the primary antibody and a subsequent reagent, if any. The secondary antibody is generally the second antibody used in an immunohistochemical procedure. The novel and unique fluorescence in situ hybridization and detection technique described herein is a method which allows the use of recombinant DNA or RNA probes with paraffin-embedded or otherwise fixed-treated samples, including for example, cells, microorganisms, or tissue sections, and is compatible with microscopic examination routinely performed in bacteriology, parasitology, histology or pathology laboratories. The present invention applies a nucleic acid probe of predetermined nucleotide sequence to the sample cells or tissue and to the examination of the sample by microscopy, for example, to determine which cells or tissues within the population contain the specific nucleic acid target sequences of interest.

Sample Preparation of Fixed Treated Tissue

Any tissue sample from a subject may be used. Examples of tissue samples that may be used include, but are not limited to, breast, prostate, ovary, colon, lung, endometrium, stomach, salivary gland or pancreas. The tissue sample can be obtained by a variety of procedures including, but not limited to surgical excision, aspiration or biopsy. The tissue may be fresh or frozen. In one embodiment, the tissue sample is fixed and embedded in paraffin or the like.

The tissue sample may be fixed (i.e. preserved) by conventional methodology [See e.g., "Manual of Histological Staining Method of the Armed Forces Institute of Pathology," 3rd edition (1960) Lee G. Luna, HT (ASCP) Editor, The Blakston Division McGraw-Hill Book Company, New York; The Armed Forces Institute of Pathology Advanced Laboratory Methods in Histology and Pathology (1994) Ulreka V. Mikel, Editor, Armed Forces Institute of Pathology, American Registry of Pathology, Washington, D.C.]. One of skill in the art will appreciate that the choice of a fixative is determined by the purpose for which the tissue is to be histologically stained or otherwise analyzed. One of skill in the art will also appreciate that the length of fixation depends upon the size of the tissue sample and the fixative used. By way of example, neutral buffered formalin, Bouin's or paraformaldehyde, may be used to fix a tissue sample.

Generally, the tissue sample is first fixed and is then dehydrated through an ascending series of alcohols, infiltrated and embedded with paraffin or other sectioning media so that the tissue sample may be sectioned. Alternatively, one may section the tissue and fix the sections obtained. By way of example, the tissue sample may be embedded and processed in paraffin by conventional methodology (See e.g., "Manual of Histological Staining Method of the Armed Forces Institute of Pathology", supra). Examples of paraffin that may be used include, but are not limited to, Paraplast, Broloid, and Tissuemay. Once the tissue sample is embedded, the sample may be sectioned by a microtome or the like (See e.g., "Manual of Histological Staining Method of the Armed Forces Institute of Pathology", supra). By way of example for this procedure, sections may range from about three microns to about five microns in thickness. Once sectioned, the sections may be attached to slides by several standard methods. Examples of slide adhesives include, but are not limited to, silane, gelatin, poly-L-lysine and the like. By way of example, the paraffin embedded sections may be attached to positively charged slides and/or slides coated with poly-L-lysine.

If so desired, the tissue sections may be deparaffinized by several conventional standard methodologies. For example, xylenes and a gradually descending series of alcohols may be used (See e.g., "Manual of Histological Staining Method of the Armed Forces Institute of Pathology", supra). Alternatively, commercially available deparaffinizing non-organic agents such as Hemo-De.RTM. (CMS, Houston, Tex.) may be used.

Preparing Cell-Lines and Tissue for Fluorescence In Situ Hybridization

The present invention is directed towards a method for preparing a sample for fluorescence in situ hybridization, comprising the steps of:

(a) pressure cooking the sample; and
(b) treating the pressure cooked sample with ammonia-ethanol and sodium borohydride.

Preferably, the pressure cooking is performed in a decloaking chamber at a temperature of about 125° C. reaching a pressure of between about 20 to about 24 PSI.

Preferably, the ammonia-ethanol is used in a concentration of about 0.25%. Preferably, the sodium borohydrate is used in a concentration of about 5%.

As will be apparent to one of skill in the art, this method is ideally suited to fixed-treated cell lines and tissue, particularly paraffin embedded tissue. In a preferred embodiment, the tissue is mammalian. In another preferred embodiment, the mammalian tissue is human.

Accordingly, the present invention is directed towards a pressure cooked composition comprising:

(a) a fixed-treated tissue;
(b) ammonia-ethanol; and
(c) sodium borohydride

In a preferred embodiment, the ammonia-ethanol concentration is about 0.25% in the pressure cooked composition. In another preferred embodiment, the sodium borohydride concentration is about 5% in the pressure cooked composition.

In one aspect of the invention, the pressure cooked composition can be used in FISH. Accordingly, in one aspect FISH further comprises a quantification step wherein an mRNA expression level is calculated as a proportion of fluorochrome signal intensity of the mRNA.

In one aspect of the invention, the pressure cooked and treated composition will display reduced autofluorescence as compared to compositions which are not so treated. In one aspect, the composition will display 5%, 10%, 20%, 30%, 40%, 50%, 60%, 70% or more of a reduction in autofluorescence.

Fluorescence In Situ Hybridization (Fish)

In situ hybridization may be performed by several conventional methodologies [See for e.g. Leitch et al. In Situ Hybridization: a practical guide, Oxford BIOS Scientific Publishers, Micropscopy handbooks v. 27 (1994)]. In one in situ procedure, fluorescent dyes (such as fluorescein isothiocyanate (FITC) which fluoresces green when excited by an Argon ion laser) are used to label a nucleic acid sequence probe which is complementary to a target nucleotide sequence in the cell. Each cell containing the target nucleotide sequence will bind the labeled probe producing a fluorescent signal upon exposure of the cells to a light source of a wavelength appropriate for excitation of the specific fluorochrome used.

Various degrees of hybridization stringency can be employed. As the hybridization conditions become more stringent, a greater degree of complementarity is required between the probe and target to form and maintain a stable duplex. Stringency is increased by raising temperature, lowering salt concentration, or raising formamide concentration. Adding dextran sulfate or raising its concentration may also increase the effective concentration of labeled probe to increase the rate of hybridization and ultimate signal intensity. After hybridization, slides are washed in a solution generally containing reagents similar to those found in the hybridization solution with washing time varying from minutes to hours depending on required stringency. Longer or more stringent washes typically lower nonspecific background but run the risk of decreasing overall sensitivity.

Probes used in the FISH analysis may be either RNA or DNA oligonucleotides or polynucleotides and may contain not only naturally occurring nucleotides but their analogs like digoxygenin dCTP, biotin dcTP 7-azaguanosine, azidothymidine, inosine, or uridine. Other useful probes include peptide probes and analogues thereof, branched gene DNA, peptidometics, peptide nucleic acid (PNA) and/or antibodies. Probes should have sufficient complementarity to the target nucleic acid sequence of interest so that stable and specific binding occurs between the target nucleic acid sequence and the probe. The degree of homology required for stable hybridization varies with the stringency of the hybridization medium and/or wash medium. Preferably, completely homologous probes are employed in the present invention, but persons of skill in the art will readily appreciate that probes exhibiting lesser but sufficient homology can be used in the present invention [see for e.g. Sambrook, J., Fritsch, E. F., Maniatis, T., Molecular Cloning A Laboratory Manual, Cold Spring Harbor Press, (1989)]. "Complementary," when referring to two nucleotide sequences, means that the two sequences of nucleotides are capable of hybridizing, preferably with less than 25%, more preferably with less than 15%, even more preferably with less than 5%, most preferably with no mismatches between opposed nucleotides. Preferably the two molecules will hybridize under conditions of high stringency.

As used herein, stringency of hybridization may be determined as follows or using other protocols known to one of skill in the art:

1) high stringency: 0.1.times.SSPE, 0.1% SDS, 65° C.
2) medium stringency: 0.2.times.SSPE, 0.1% SDS, 50° C.
3) low stringency: 1.0.times.SSPE, 0.1% SDS, 50° C.

It is understood that equivalent stringencies may be achieved using alternative buffers, salts and temperatures.

One of skill in the art will appreciate that the choice of probe will depend on, for example, the genetic expression or abnormality of interest. Genetic abnormalities that can be detected by this method include, but are not limited to, amplification, translocation, deletion, addition and the like. Probes may also be generated and chosen by several means including, but not limited to, mapping by in situ hybridization, somatic cell hybrid panels, or spot blots of sorted chromosomes; chromosomal linkage analysis; or cloned and isolated from sorted chromosome libraries from human cell lines or somatic cell hybrids with human chromosomes, radiation somatic cell hybrids, microdissection of a chromosome region, or from yeast artificial chromosomes (YACs) identified by PCR primers specific for a unique chromosome locus or other suitable means like an adjacent YAC clone. Probes may be, for example, genomic DNA, cDNA, or RNA cloned in a plasmid, phage, cosmid, YAC, Bacterial Artificial Chromosomes (BACs), viral vector, or any other suitable vector. Probes may be cloned or synthesized chemically by conventional methods.

Probes are preferably labeled with a fluorophore. Examples of fluorophores include, but are not limited to, rare earth chelates (europium chelates), Texas Red, rhodamine, fluorescein, dansyl, phycocrytherin, phycocyanin, spectrum orange, spectrum green, and/or derivatives of any one or more of the above. Multiple probes used in the assay may be labeled with more than one distinguishable fluorescent or pigment color. These color differences provide a means to identify, for example, the hybridization positions of specific probes. Moreover, probes that are not separated spatially can be identified by a different color light or pigment resulting from mixing two other colors (e.g., light red+green=yellow) pigment (e.g., blue+yellow=green) or by using a filter set that passes only one color at a time.

Probes can be labeled directly or indirectly with the fluorophore, utilizing conventional methodology. Additional probes and colors may be added to refine and extend this general procedure to include more genetic abnormalities or serve as internal controls.

Analysis of Fluorescence and Technical Applications

After processing for FISH, analysis may be performed by standard techniques of fluorescence [see for e.g. Ploem and Tanke Introduction to Fluorescence Microscopy, New York, Oxford University Press (1987)].

In order to correlate cellular morphology with FISH, one may use a computer-driven, motorized stage which stores location of coordinates. This may be used to evaluate the same area by two different analytical techniques. For example, color images of the morphologically stained areas may be captured and saved using a computer-assisted cooled CCD camera. The same section may be subsequently taken through the FISH procedure, the stored locations recalled, and the designated areas scored for the presence of fluorescent nuclear signals.

Typically, hundreds of cells are scanned in a tissue sample and quantification of the specific target nucleic acid sequence is determined in the form of fluorescent spots, which are counted relative to the number of cells. Deviation of the number of spots in a test cell from a norm may be indicative of a malignancy or a predisposition to a malignancy, disease, or other abnormality. The relative number of abnormal cells to the total cell sample population may also indicative of the extent of the condition or abnormality. In addition, using family health histories and/or genetic screening, it is possible to estimate the probability that a particular subject has for developing certain types of disease. Those subjects that have been identified as being predisposed to, for example, developing a particular form of disease can be monitored or screened to detect early evidence of disease. Upon discovery of such evidence, early treatment can be undertaken to combat the disease. Similarly, those subjects who have already developed, for example, a malignancy and who have been treated to remove the cancer or are otherwise in remission are particularly susceptible to relapse and reoccurrence, including the metastasis of tumors. Such subjects can be monitored and screened using the presently disclosed methods to detect evidence of metastasis and upon discovery of such evidence, immediate treatment can be undertaken to combat the disease.

Thus, in infected whole blood smears, cell lines or tissue sections, endogenous nucleic acids or nucleic acids of pathogenic organisms such as bacteria, virus, protozoan, or fungi, can be detected within the infected cells. Such methods provide useful diagnostic and scientific information since the presence or absence of a specific nucleic acid can directly or indirectly correlate with one or more cells of observable structure and morphology, and, in this way, provide a basis for clinical diagnosis and prognosis.

For example, scientists, physicians and other investigators attempt to develop compounds or other agents that will have effects on specific molecular pathways in cells that will have a therapeutic effect on disease. The therapeutic action of many of these compounds is expected to result in (directly or indirectly) either suppressing the expression of a gene(s) or, alternatively, the promotion of the expression of that gene(s). In turn, the targeted gene(s), through its suppression or promotion, can either suppress or promote the expression of other genes in molecular pathways that influence the course of disease. Therefore, in order to assess the effect(s) of a putative therapeutic compound or identify toxic effects of a test compound, it would useful to determine if that compound does indeed have the effect of suppressing or promoting genes that are in molecular pathways believed to be involved in the pathogenesis of disease or, in the case of a potential toxic compound, it would be useful to determine if that compound is involved in pathways related to toxic responses.

The earliest expression of a gene is pre-mRNA, with the secondary expression resulting in the processing of that pre-mRNA to create mRNA. Therefore, it would be useful to measure pre-mRNA and/or mRNA related to the genes of interest in disease pathogenesis. Such measurements could indicate if a putative compound may indeed work and provide investigators with evidence of whether to proceed with the discovery and development process regarding a specific compound or terminate that process.

The methods of this invention are suitable for use with any specimen obtained from a patient including but not limited to, whole blood, serum, plasma, sputum, urine, breast milk, cerebral spinal fluid, and tissue. These methods are also suitable for detection of a pathogen within the cells of an insect vector. The sample is deposited onto the slide by standard means, and is then fixed onto the slide. The purpose of fixing cells or tissue is to preserve the morphology of the cells or tissue such that RNA is retained within the cellular matrix under the rigorous conditions experienced during in situ hybridization. The preferred method thus utilizes a fixative which is able to preserve and retain nucleic acids of the cell and at the same time cross-link and/or precipitate the proteins in the cellular matrix such that the cell or tissue remains substantially in open configuration for probe penetration and subsequent hybridization.

There are three main ways in which cells and tissues may be processed to retain their structural organization for subsequent experimentation. These are fixation by cross-linking, fixation by precipitation, and fixation by freezing (cryofixation). Cryofixation, is probably the best technique for cellular preservation, and is often employed for electron microscopy for this reason. It involves rapidly freezing the cells or tissues on a cooled block of heat-conductive metal or rapid plunging into a cold medium, such as liquid nitrogen or freon. Following freezing, the samples may then be treated with a cross-linking reagent, discussed below, in a process called 'freeze substitution'. The disadvantages of cryofixation are that it typically requires specialized equipment usually unavailable in most laboratories.

The selection of a specific fixation protocol will be dictated by several factors. First, the fluorescent probe to be used may place restrictions on which treatment may be necessary (i.e. some fixations prevent binding of certain dyes). Second, the size or thickness of a given sample may preclude the use of certain fixatives due to permeability (i.e. a fixative that is unable to penetrate into thick samples will only preserve the outer layers).

Fixation by cross-linking is a method commonly used for fluorescence microscopy. It involves treating specimens with reagents that penetrate into the cells and tissues and form covalent cross-links between intracellular components. The most commonly used cross-linking agents are aldehydes, which form covalent bonds between adjacent amine-containing groups through Schiff acid-base reaction. These bonds form both inter- and intra-molecularly and are, therefore, very effective fixatives for proteins and nucleic acids. The two most frequently used aldehydes are formaldehyde and glutaraldehyde. Both fixatives have advantages and disadvantages, which will be discussed below. Other alde hydes, such as acrolein, have been used historically, but do not preserve samples as well.

Glutaraldehyde is a four carbon molecule terminated at both ends by aldehyde groups. It is an extremely efficient fixative, and is widely used by light and electron microscopy for its efficacy in preserving cellular structure. Use of glutaraldehyde does have certain disadvantages, however. First, its comparatively high molecular weight limits its ability to diffuse into thick specimens, such as tissue sections or embryos. This is further exacerbated by the fact that as the tissue is cross-linked by the fixative, its ability to penetrate over time diminishes. For such samples, formaldehyde may be a better option. Second, free aldehyde groups fluoresce efficiently at the same wavelengths as many of the fluorescent probes employed by biologists. As glutaraldehyde possesses two functional groups per molecule, background autofluorescence may be a significant problem in fixed tissues, effectively lowering the probe's signal to noise. This problem may be circumvented by using relatively low concentrations of glutaraldehyde (i.e. less than 1%). Unreacted aldehydes may also be quenched by treating fixed samples with reducing agents, such as sodium borohydride, to reduce free aldehyde groups to alcohols, or by reacting them with exogenous amine-containing reagents, such as ammonium chloride or glycine. In a preferred embodiment of the present invention, the fixed tissue is treated with sodium borohydride to quench autofluorescence.

Formaldehyde is probably the most commonly used cross-linking fixative for biological samples. It has a single aldehyde-containing carbon and exists as a gas. Formaldehyde does not cross-link as effectively as glutaraldehyde, and for this reason is rarely used by-itself for electron microscopy. However, its small molecular weight allows it to penetrate cells and tissues rapidly, making it a choice fixative for thicker samples and autofluorescence of unreacted aldehyde groups is not usually a problem.

Methods for detecting a target nucleic acid fragment directly from a specimen are comprised of multiple steps which are typically performed in the following order. A specimen, usually obtained from a patient, is fixed and embedded in paraffin. The embedded tissue may be sectioned for Tissue-FISH. The sample is treated in keeping with the inventive method (i.e. the sample is pressure cooked and treated with ammonia-ethanol and sodium borohydride). The nucleic acids of the sample are then incubated with a labeled probe specific for the target nucleic acid fragment, under conditions appropriate for hybridization. The probe is comprised of a nucleic acid sequence which is complementary to the target nucleic acid on the tissue under stringent conditions. The probe is then visualized and quantified if necessary. This information can then be compared to a baseline or to another cell or any other desired application as would be apparent to one of skill in the art.

The quantity of the total probe used is a predetermined amount which should exceed the estimated amount of the available target believed to be within the sample (about 100:1) in order to drive the hybridization reaction efficiently and to promote a high rate of probe:target annealing. The labeled probe is incubated with the nucleic acids of the fixed sample. In one embodiment, the labeled probe is generally added in solution onto the sample. Conditions appropriate for hybridization are solutions which provide the appropriate buffered environment. The specific concentration of hybridization buffer varies with the nucleic acid sequence and length of the probe. The exact concentration of buffer used is dependent on the Tm of the probe, probe sequence, probe length, and hybridization temperature, and can be determined by one of skill in the art through the course of no more than routine experimentation.

After hybridization is complete, the non-hybridized probe is typically rinsed from the sample, generally by applying a series of stringent washes with a wash buffer. It is within the means of those skilled in the art to determine appropriate wash buffers. In one embodiment, the wash buffer is 0.3 M sodium chloride, 0.03 M sodium citrate, and 0.5% NP40. In another embodiment, the wash buffer is phosphate buffered saline (PBS). In a further embodiment, the wash is formamide/sodium citrate.

After rinsing, the sample may be counterstained to allow the visualization of organisms within the cells, which contain the hybridized probes. This staining step is generally applied when a fluorescent-labeled probe is used to detect nucleic acids, which are specific for a pathogen. Counterstaining the cells or tissue concurrently with the in situ hybridization assay enhances the method by allowing a clearer determination of the location of the target nucleic acid within the sample. Such information helps, for example, to provide a clearer determination of background hybridization. In one embodiment, the counterstain is DAPI, Toto-3, To-pro-3, Sytox Green, Yoyo-1, Propidium Iodide, Bobo-3 or Evans Blue.

In one embodiment, any labeled probe that is hybridized to the nucleic acid of the fixed sample is then visually detected by microscopy. The presence of labeled probe within the sample is an indication of the presence of the target nucleic acid fragment. The sensitivity of this method has been determined to detect as little as 10 copies of target nucleic acid.

It should be appreciated that the use of formamide or GuSCN in the hybridization fluid allows hybridization to be carried out at a much lower temperature than standard hybridization protocols. Hybridization of an average probe specifically to the target (and not to host cells) in aqueous hybridization fluid such as sodium chloride would generally require a temperature of 60–65° C. The same hybridization performed at 42° C. in hybridization buffer described above, would provide specificity.

The probe is detected by means suitable for the specific moiety used to label the probe. In one embodiment, the marker moiety is a fluorophore. In a preferred embodiment, the fluorophore is FITC, Fluo-3, 5 hexadecanoyl fluorescein, Cy2, fluorX, Cy3, Cy3.5, Cy5, Cy5.5, Cy7, fluorescein and Texas Red. For example, the preferred method for detecting a fluorescent-labeled probe, employs special filters such as a blue filter (fluorescent labeled probe) and a green filter (for rhodamine-X or Texas red labeled probe).

The methods of this invention may be used for simultaneous detection of different transcripts in a single clinical sample by performing one reaction with a labeled probe, which is comprised of a plurality of different nucleic acid sequences, each labeled with a different marker moiety. For simultaneous detection, the probes that are specific for the different nucleic acids commonly present in a clinical specimen can be designed such that the Tm values of all the probe sequences are very similar. Each specific probe is then labeled with a different detectable moiety (e.g. different fluorescent moieties). Hybridization is performed with the multiple components of the probe. The hybridized sample is processed as described above and the sample is observed by means appropriate for detection of the different labeled probes (e.g. viewed using appropriate filters if different fluorescent moieties are used) to detect which transcripts are detected in the sample.

It will be recognized by practitioners ordinarily skilled in this art that the novel in situ hybridization protocol described herein is compatible with all previously known methods of detection as well as the one described herein. It is expected that the reagents described in the present invention may be provided in a kit form to practice the protocol, which has been optimized for simplicity and for compatibility with a wide variety of detection methods. It is also expected that such prepared kits containing specifically prepared reagents and probes, will be applicable in clinical/diagnostic laboratories, where the ability to detect the presence or absence of specific nucleic acids would serve to positively or negatively identify pathological states characterized by the presence of specific genes. In a preferred embodiment, such methods would be designed for use with fixed treated tissue and would comprise reagents necessary therefore.

Accordingly, in one embodiment, the invention provides a method for identifying a potential therapeutic agent which modulates a level of a gene's expression in a tissue, the method comprising:

(a) preparing at least a first and second sample from at least a first and second tissue according to the inventive process described herein, wherein the samples are identical with the exception that the first tissue has been sampled from a cell-line, animal or human that has been treated with the agent whereas the second tissue has been sampled from a cell-line, animal, or human that has not;

(b) detecting the level of the gene's transcription in the at least first and second tissue using FISH, wherein a difference in the detected levels indicates that the agent modulates the level of the gene's expression. In one preferred embodiment, the modulation of the gene's expression is comprised in a pathway associated with therapeutic effects on the cell-line, animal, or human. Identification of a favorable response to a particular agent may be critical in assessing potential therapeutic effects of candidate therapeutic agents. In another preferred embodiment, the modulation of the gene's expression is comprised in a pathway associated with toxic effects on the cell line, animal, or human. Identification of a toxic response to a particular agent may be critical in assessing potential detrimental effects of candidate therapeutic agents.

Unless otherwise defined, all technical and scientific terms used herein have the same meaning as commonly understood by one of ordinary skill in the art to which this invention belongs. In case of conflict, the present application, including definitions will control. All publications, patent applications, patents, and other references mentioned herein are incorporated by reference.

Although methods and materials similar or equivalent to those described herein can be used in the practice or testing of the invention, preferred methods and materials are described below. The materials, methods, and examples are illustrative only and not intended to be limiting. Other features and advantages of the invention will be apparent from the detailed description and the claims.

EXAMPLES

Example 1

In Situ Hybridization

Pretreatment

5 μm paraffin-embedded sections were dried at 37° C. for about 1 hour and then transferred to a decloaker chamber for 30 minutes where they were deparaffinized and antigen-retrieved using a solution that allows both steps to occur at the same time. The slides were then washed in PBS for 10 minutes, incubated for 20 minutes in 0.25% ammonia-ethanol at room temperature (RT), and then incubated for 50 minutes in 5% sodium borohydride in PBS at RT. The slides were then washed twice with tap water and then in PBS for 5 minutes.

Hybridization

The slides were incubated for at least 15 minutes in a prehybridization solution of formamide/2×SSC at RT. The slides were then hybridized with a specific set of probes at 37° C. in a humidity chamber from 3 hours to overnight. The slides then underwent several post-hybridization washes which included:

Formamide/2×SSC for 20 minutes at 37° C.
1×SSC at RT on a shaker for 15 minutes
0.5×SSC at RT on a shaker for 15 minutes The slides were then washed in PBS/MgCl$_2$ for 5 minutes and then the nuclei were counterstained using a DAPI solution (Blue). The slides were rinsed in PBS/MgCl$_2$ for 5 minutes to remove the excess solution, and then mounted and coverslipped using an antifade mounting solution. The slides were kept at −20° C. until the actual reading under the fluorescent microscope.

We claim:

1. A method for preparing a mammalian cell-line and/or mammalian tissue sample for in situ hybridization, comprising the steps of:
   (a) pressure cooking the sample in a decloaking chamber at a temperature of about 125° C. reaching a pressure of between about 20 to about 24 PSI; and
   (b) treating the pressure cooked sample with ammonia-ethanol in a concentration of about 0.25% and sodium borohydride in a concentration of about 5%.

2. The method of claim 1 wherein the sample is fixed-treated.

3. The method of claim 2 wherein the fixed-treated sample is paraffin embedded.

4. The method of claim 1 wherein the tissue or the cell is human.

5. A pressure cooked composition comprising:
a fixed-treated tissue according to claim 1.

6. The pressure cooked composition according to claim 5, wherein the fixed-treated tissue is paraffin embedded.

7. A method for reducing autofluorescence when performing FISH on a fixed treated tissue sample, the method comprising
   (a) pressure cooking the sample in a decloaking chamber at a temperature of about 125° C. reaching a pressure of between about 20 to about 24 PSI; and
   (b) treating the pressure cooked sample with ammonia-ethanol in a concentration of about 0.25% and sodium borohydride in a concentration of about 5%.
wherein both steps are performed on the sample prior to performing FISH.

* * * * *